US010852286B2

(12) United States Patent
Allen et al.

(10) Patent No.: US 10,852,286 B2
(45) Date of Patent: *Dec. 1, 2020

(54) READY TO USE PORCINE VACCINE

(71) Applicant: Intervet Inc., Madison, NJ (US)

(72) Inventors: Michelle Allen, DeSoto, KS (US); Mark Garrett, Overland Parks, KS (US); Urs Peter Bruderer, Kleve (DE); Martinus Antonius Johannes Thijssen, Groeningen (NL)

(73) Assignee: Intervet, Inc., Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/670,513

(22) Filed: Oct. 31, 2019

(65) Prior Publication Data

US 2020/0080981 A1   Mar. 12, 2020

Related U.S. Application Data

(60) Division of application No. 16/129,144, filed on Sep. 12, 2018, now abandoned, which is a division of application No. 15/426,206, filed on Feb. 7, 2017, now Pat. No. 10,101,310, which is a division of application No. 14/320,840, filed on Jul. 1, 2014, now Pat. No. 9,599,607, which is a division of application No. 13/759,620, filed on Feb. 5, 2013, now Pat. No. 8,802,378, which is a continuation of application No. 12/875,618, filed on Sep. 3, 2010, now Pat. No. 8,546,149.

(60) Provisional application No. 61/377,485, filed on Aug. 27, 2010.

(30) Foreign Application Priority Data

Sep. 29, 2010 (EP) .................................. 10181634

(51) Int. Cl.
| | |
|---|---|
| *G01N 33/53* | (2006.01) |
| *A61K 39/12* | (2006.01) |
| *G01N 33/15* | (2006.01) |
| *G01N 33/569* | (2006.01) |
| *G01N 33/543* | (2006.01) |

(52) U.S. Cl.
CPC ............ *G01N 33/15* (2013.01); *A61K 39/12* (2013.01); *G01N 33/5306* (2013.01); *G01N 33/54306* (2013.01); *G01N 33/56933* (2013.01); *G01N 33/56983* (2013.01); *G01N 2333/01* (2013.01); *G01N 2333/30* (2013.01); *G01N 2469/10* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 4,459,359 | A | 7/1984 | Neurath |
| 4,703,001 | A | 10/1987 | Vodian et al. |
| 8,263,415 | B2 | 9/2012 | Berling et al. |
| 8,444,989 | B1 | 5/2013 | Ohnesorge et al. |
| 9,125,886 | B2 | 9/2015 | Nitzel et al. |
| 2009/0317423 | A1 | 12/2009 | Roof et al. |

FOREIGN PATENT DOCUMENTS

| | | |
|---|---|---|
| CN | 101583872 A | 11/2009 |
| JP | 2006311824 A | 11/2006 |
| WO | 9628472 A1 | 9/1996 |
| WO | 199926664 A1 | 6/1999 |
| WO | 2003003941 A2 | 1/2003 |
| WO | 2004058142 A2 | 7/2004 |
| WO | 2007103042 A2 | 9/2007 |
| WO | 2009126356 A2 | 10/2009 |
| WO | 2013152081 A1 | 10/2013 |
| WO | 2014/105672 A1 | 7/2014 |

OTHER PUBLICATIONS

Ahmad, I. et al, Sensitivity and Specificity of Mycoplasma gallisepticum Agglutination Antigens Prepared from Medium with Artificial Liposomes Substituting for Serum, Avian Diseases, Jul.-Sep. 1988, pp. 519-526, vol. 32, No. 3.
Allan and Ellis, Porcine Circoviruses: a review, J. Vet Diagn. Invest., 2000, 3-14, 12(1).
Allan et al., Discovery and evolving history of two genetically related but phenotypically different viruses, porcine circoviruses 1 and 2, Virus Research, 2012, 4-9, 164(1-2).
Armstrong, C.H., Porcine Mycoplasmas, Mycoplasmosis in Animals:Laboratory Diagnosis, 1994, Ch 6, 1st Ed., 6.
Committee for Veterinary Medicinal Products, EMEA: Notice for Guidance: Requirements for Combined Veterinary Vaccines, effective Jan. 1, 2001, pp. 1-6.
Coombes, L. et al., Development and use of a novel in vitro assay for testing of diphtheria toxoid in combination vaccines, Journal of immunological methods, Jun. 18, 2009, 142-149, 350, EP.
Declaration by Dr. Rhona Banks dated Nov. 7, 2016.
Declaration of Gregory P. Nitzel dated Nov. 10, 2016 and Curriculum Vitae in Annex.
Declaration under 37 C.F.R. §132 dated Mar. 19, 2015, signed by Gregory P. Nitzel. Note: USPTO Filing date is Mar. 26, 2013.
Djordjevic, S.P., et al., Serum and mucosal antibody responses and protection in pigs vaccinated against Mycoplasma hyopneumoniae with vaccines containing a denatured membrane antigen pool and adjuvant, Aust. Vet. J., 1997, pp. 504-511, vol. 75.
Dodig, S., Interferences in quantative immunochemical methods, Biochemica Medica, 2009, pp. 50-62, 19(1).
Durkin, M et al., Detection of Coccidioides Antigenemia following Dissociation of Immune Complexes, Clinical and Vaccine Immunology, 2009, pp. 1453-1456, vol. 16, No. 10.

(Continued)

*Primary Examiner* — Jennifer E Graser
(74) *Attorney, Agent, or Firm* — Michael D. Davis

(57) ABSTRACT

The invention relates to certain methods for the determination of an antigen content of a first antigen in a mixture comprising two or more antigens. The invention also relates to a potency test for an antigen in a combination vaccine. The method allows the determination of the antigen content in a mixture additionally comprising antibodies that are capable of binding with the antigen.

16 Claims, 4 Drawing Sheets

(56) References Cited

OTHER PUBLICATIONS

European Search Report, application No. 10181634.6, dated Mar. 3, 2011.
Excerpt from file history U.S. Appl. No. 13/759,620 submitted by Opponent 1.
Excerpt from the file history of U.S. Appl. No. 14/320,840 submitted by Opponent 2.
Excerpt from the file history of U.S. Appl. No. 14/320,840 submitted by Opponent 1.
Experimental data on antigen content determination failures submitted by Opponent 1, 2 pages.
Fattom et al., EpitopicOverload at the Site of Injection May result in Suppression of the Immune Response to Combined Capsular Polysaccharide Conjugate Vaccines, Vaccine, 1999, 126-133, 17.
Freundt, E.A., Methods in Mycoplasmology, Culture Media for Classic Mycoplasmas, 1983, 127-134, 1-C7.
Friis, N.F., Mycoplasma suipneumoniae and mycoplasma flocculare in the growth precipitation test, Acta vet. Scand., 1977, pp. 168-175, 18.
Friis, N.F., Some Recommendations Concerning Primary Isolation of Mycoplasma suipneumoniae and Mycoplasma flocculare, Nord. Vet.-Med., 1975, 337-339, 27.
Goodwin, R.F.W. et al., Production of enzootic pneumonia in pigs with Mycoplasma suipneumoniae grown in embryonated hens' eggs, Br. J. Exp. Pathol., 1968, pp. 431-435, vol. 49.
Hwang et al., Optimization of cluture media of pathogenic Mycoplasma hyopneumoniae by a response surface methodology, Journal of Veterinary Science, 2010, 327-332, 11(4).
International Search report Application No. PCT/EP2011/064702, dated Nov. 15, 2011.
Kricka, L.J., Interferences in Imunoassay—Still a Threat, Clinical Chemistry, 2000, pp. 1037-1038, 46 (8).
Kroll, Mid. and Elin R.J., Interference with Clinical Laboratory Analyses, Clin. Chem., 1994, pp. 1996-2005, 40/11.
Lab notebook pages, not prior art, from 2005, submitted by Opponent 2.
Magar, R. et al., Retrospective serological survey of antibodies to porcine circovirus type 1 and 2, The Canadian Journal of Veterinary Research, 2000, pp. 184-186, 64.
McNeilly, et al., Evaluation of a porcine circovirus type 2-specific antigen-capture enzyme-linked immunosorbent assay for the diagnosis of postweaning multisystemic . . . , J. Vet. Diagn. Invest., 2002, pp. 106-112, 14.
Nawagitgul, P. et al., Modified Indirect Porcine Circovirus (PCV) Type 2-Based and Recombinant Capsid Protein (ORF2)-Based Enzyme-Linked Immunosorbent Assays for Detection of Antobodies to PCV, Clinical and Diagnostic Laboratory Immunology, Jan. 2002, pp. 33-40, vol. 9, No. 1.
Nitzel, G.P., Declaration Under 37 C.F.R. §1,132 of Gregory P. Nitzel dated Mar. 19, 2015; Submitted in the file history of U.S. Appl. No. 13/850,331, filed Mar. 26, 2013; 2015, pp. 1-12.
Opriessnig, T. et al., Porcine circovirus type 2-associated disease: Update on current terminolory, clinical manifestations, pathogenesis, diagnosis, and intervention strategies, J. Vet. Diag. Invest., 2007, pp. 591-615, 19.
Patton, A et al., An acid dissociation briding ELISA for detection of antibodies directed against therapeutic proteins in the presence of antigen, Journal of Immunological methods, 2005, pp. 189-195, vol. 304.
Product Leaflet 'FLEXcombo' for Boehringer Ingelheim's Porcine Circovirus Vaccine Ingelvac CircoFLEX, unknown publication date, submitted by Opponent 2.
Ramírez, A.S., et al., A semi-defined medium without serum for small ruminant mycoplasmas, The Veterinary Journal, 2008, pp. 149-152, 178.
Selby, C., Interference in immunoassay, Ann. Clin. Biochem., 1999, pp. 704-721, 36.
Sesardic, D. et al., Non-pertussis components of combination vaccines: problems with potency testing, Biologicals, 1999, pp. 177-181, 27, US.
Sheldrake, R.F. and Romalis, L.F., Evaluation of an enzyme-linked immunosorbent assay for the detection of Mycoplasma hyopneumoniae antibody in porcine serum, Aust. Vet J., 1992, pp. 255-258, vol. 69, No. 10.
Vidor, E., The nature and consequences of intra- and inter-vaccine interference, J. Comp. Path., 2007, pp. S62-S66, vol. 137.
Walker, I.W. et al., Development and application of a competitive enzyme-linked immunosorbent assay for the detection of serum antibodies to porcine cirovirus type 2, J. Vet. Diagn. Invest., 2000, pp. 400-405, 12.

Fig. 1. Demonstration of PCV-antibody complexes

Fig. 2. Influence of acid concentration
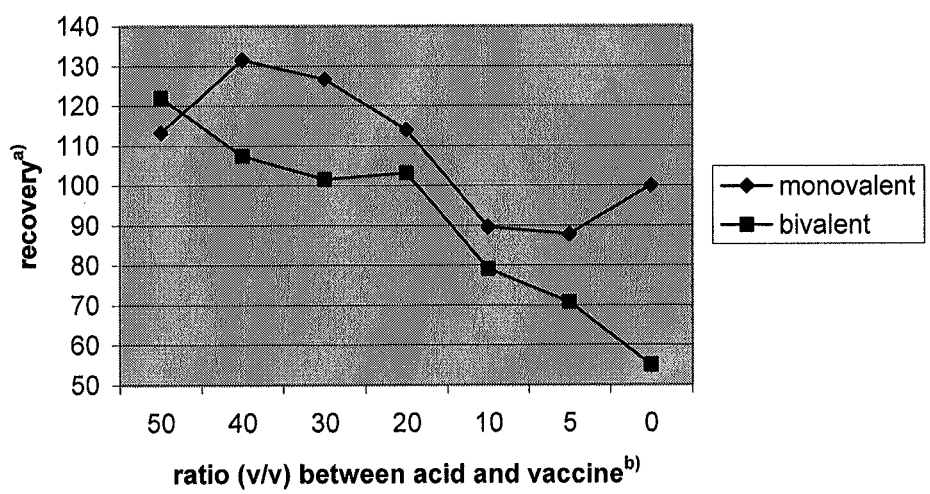

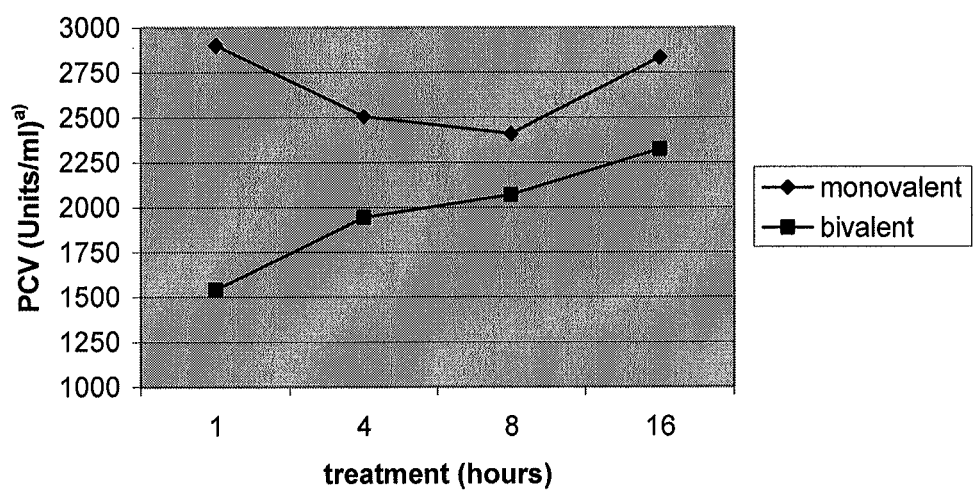
Fig. 3. Influence of treatment time

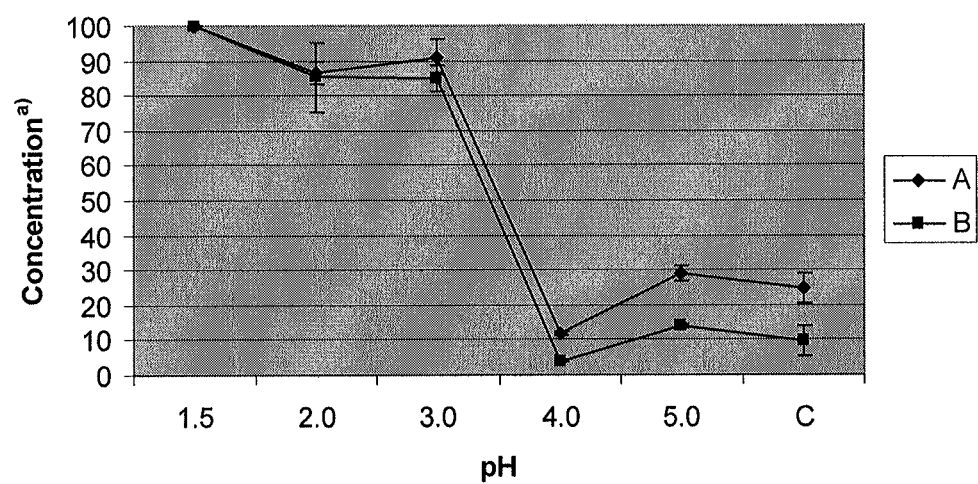
Fig. 4. Influence of pH

READY TO USE PORCINE VACCINE

CROSS-REFERENCE TO RELATED APPLICATIONS

This application is a Divisional application of U.S. Ser. No. 16/129,144, filed on Sep. 12, 2018, which is a Divisional application of U.S. Ser. No. 15/426,206, filed on Feb. 7, 2017, now U.S. Pat. No. 10,101,310, granted Oct. 16, 2018, which is a Divisional application of U.S. Ser. No. 14/320, 840, filed on Jul. 1, 2014, now U.S. Pat. No. 9,599,607, granted Mar. 21, 2017, which is a Divisional application of U.S. Ser. No. 13/759,620, filed on Feb. 5, 2013, now U.S. Pat. No. 8,802,378, granted Aug. 12, 2014, which is a Continuation application of non-provisional application U.S. Ser. No. 12/875,618, filed on Sep. 3, 2010, now U.S. Pat. No. 8,546,149, granted on Oct. 1, 2013, that claims priority under 35 U.S.C. § 119 (e) of provisional application U.S. Ser. No. 61/377,485, filed on Aug. 27, 2010, the contents of all of which are hereby incorporated by reference in their entireties.

FIELD OF THE INVENTION

The invention relates to certain methods for the determination of an antigen content of a first antigen in a mixture comprising two or more antigens. The invention also relates to a potency test for an antigen in a combination vaccine.

BACKGROUND OF THE INVENTION

Vaccines comprising a combination of protective antigens derived from different pathogenic organisms have multiple obvious benefits, both for the recipient- and manufacturer of the vaccine. In particular, combination- or multivalent vaccines offer increased ease of administration and greater comfort and convenience to the patient by reducing the number of injections required and possibly the number of attendances. They are also more economical to manufacture and administer because of savings on processing of combined bulk material, containers, packaging, distribution and injection equipment.

In the field of human health combination vaccines are often used in the context of infant vaccination. Combination vaccines such as DTP (diphtheria, tetanus and pertussis), with or without inactivated poliomyelitis and MMR (measles, mumps and rubella) have been in use for many years and new antigens have been added to this combination during the last years.

Also in the field of animal health combination vaccines are commonly used. In particular vaccines of poultry, swine, ruminants and companion animals are, more often than not, based on a combination of multiple antigens. Examples of such vaccines are combination vaccines against canine distemper, hepatitis, parainfluenza type 2, parvovirus, leptospira and rabies virus for dogs, rotavirus, coronovirus and *E. coli* for cattle, Newcastle disease virus, infectious bronchitis, infectious bursal disease, swollen head syndrome and egg drop syndrome for poultry.

A vaccine batch may be released for sale only after a license or marketing authorization has been issued. In addition, each subsequent batch of such an authorized vaccine batch has to be formally released in compliance with the rules of a state or number of states concerned. This release may be permitted on the authority of the manufacturer after satisfactory completion of the prescribed batch testing. Therefore, to guarantee that each and every batch of vaccine will have its intended effect, a manufacturing process of consistent quality has to be in place, and the application of a potency test is an essential element of such a process.

Presently, different test methods, such as assays of physiochemical properties, antigenicity, immunogenicity, infectivity and protection against infection or disease, are used to measure vaccine potency. Their application depends on the nature of the vaccine antigens and the purpose of the test. In live vaccines, potency can be based on the number of organisms present in the vaccine (titre). In the case of inactivated vaccines, the potency is often determined by measuring the immune response in the target animal species or in another species, e.g. mice or rats. Alternatively, the potency of an inactivated vaccine can be based on its antigenicity by measuring the quantity of the antigen present (antigen mass), using immuno assays that employ specific antibodies, such as an ELISA (enzyme-linked immunosorbent assay).

BRIEF SUMMARY OF THE INVENTION

The inventors have identified an unexpected interaction between a specific antigen and another component in a combination vaccine after mixing the compositions comprising the antigen and the other component, respectively. Accordingly, the invention provides methods for the determining the antigen content of a first antigen in a mixture comprising two or more antigens. The invention also provides a potency test for an antigen in a combination vaccine. The methods provided herein further allow the determination of the antigen content in a mixture additionally comprising antibodies that are capable of binding with that antigen.

BRIEF DESCRIPTION OF THE FIGURES

FIG. 1 depicts a titration of a monovalent (♦) vaccine containing PCV-2 and a bivalent (■) vaccine containing PCV-2 and *M. hyo.* demonstrating the existence of PCV-antibody complexes.

FIG. 2 shows the influence of acid concentration on viral antigen-antibody complexes by varying the ratio (v/v) between 0.1M citric acid and monovalent (♦) or bivalent (■) vaccine. a) Recovery (%) was based on untreated monovalent vaccine measured by ELISA as described in Example 1 below. b) Ratio (v/v) between acid and vaccine during the acid treatment as described in Example 4 below.

FIG. 3 shows the influence of the time of treatment on the PCV units/ml for the monovalent (♦) and bivalent (■) vaccines. a) Units/ml determined by ELISA as described in Example 1.

FIG. 4 shows the influence of pH assessed by acid treatments at different pH's. a) 5 independent PCV batches were each mixed with one out of two, [A, B] independent *M. hyo* batches. All 10 preparations were acid treated as described in Example 4 below, either with 0.1M citric acid or with 0.1M citric acid adjusted with sodium acetate to pH 2, 3, 4, or 5, or with buffer (C=control). The concentrations are expressed as percentages of the concentrations obtained by the standard treatment (0.1M citric acid, pH 1.5). Data are shown as the mean±Std of the 5 PCV batches combined either with *M. hyo* batch A (♦) or B(■).

DETAILED DESCRIPTION OF THE INVENTION

Although, pharmacopeial requirements for the individual antigen components of combination vaccines provide a starting point to establish a relevant and effective potency test, problems resulting from interaction between the various components in more complex combination vaccines are well known (Vidor, J. Comp. Path. 137, 62-66, 2007; Sesardic et al., Biologicals 27, 177-181, 1999). Each combination vaccine is comprised of a unique aggregation of active components excipients, and residual substances. Any of these materials may interfere with accurate measurement of the potency of a given active component. Interference with an antigen's antigenicity or immunogenicity may be caused by the nature of the other antigens present, their quality, quantity or ratio, the adjuvant, preservative, stabilizer, pH, isotonicity of the vaccine etc.

Surprisingly, however, it has been found that the antigenicity of a first antigen, in a mixture of a composition comprising the first antigen and a composition comprising a second antigen, is affected by the presence of antibodies that bind to this first antigen thereby forming an antigen-antibody complex and that these antibodies can originate from the composition comprising the second antigen. Examples 1 and 2 show the problem that an antigen can be inefficiently detected in mixtures of compositions comprising different antigens and that antigen-antibody complexes can be formed in such mixtures wherein the antibodies orginate from a composition different from the composition comprising the antigen to be detected. Moreover, it has been found that the dissociation of the antigen-antibody complexes results in a recovery of the antigenicity of the first antigen. The presence of such interferring antibodies can be explained by the necessity of culturing certain micro-organisms (second antigen) in vitro in the presence of serum derived from animals and that these animals from which the serum is harvested are infected by a micro-organism that evokes antibodies against the first antigen. The interference of these antibodies with the antigenicity of the first antigen in the mixture affects the quantification of the first antigen in immunoassays, such as potency tests for releasing vaccine batches for sale.

Briefly, the invention relates to a method for the determination of an antigen content of a first antigen in a mixture of at least a composition comprising the first antigen and a composition comprising a second antigen.

The invention relates to such a method wherein the composition comprising the second antigen also comprises antibodies that are capable of binding with the first antigen.

The invention also relates to a method for the determination of an antigen content of a first antigen in a mixture of at least a composition comprising the first antigen and a composition comprising (i) a second antigen and (ii) antibodies that are capable of binding with the first antigen, the method comprising the steps of:

A dissociating antigen-antibody complexes in the mixture, formed between the first antigen and the antibodies, and
B determining the antigen content of the first antigen by means of an immunoassay.

The design of the immunoassay may vary and can be similar to those immunoassays which are commonly used in the art for quantifying viral- or bacterial antigens in samples. For example, the assay may be based upon a competition- or direct reaction. Furthermore, protocols may use solid supports, such as microtitre plates. The detection of the antigen may involve the use of (directly or indirectly) labelled antibodies specific for the first antigen (detection antibodies) and the labels may be enzymes, fluorescent-, chemilumiscent-, radioactive- or dye molecules. The detection antibodies may be monospecific polyclonal or monoclonal antibodies. Typical immunoassays to be used in a method according the invention are described in standard laboratory text books, such as, Antibodies: A Laboratory Manual, eds.: Harrlow and Lane, Cold Spring Harbor Laboratory Press, 1988. Examples of such tests are agglutination assays, ELISA and AlphLISA.

The antigens may be any kind of antigen, but preferably are derived from a micro-organism pathogenic to humans or animals. In particular, the antigens are derived from a virus or bacterium.

In general, the term antigen refers to a composition of matter that comprises at least one epitope that can induce, stimulate or enhance an immune response when administered to a human or animal.

The antigen can be the whole pathogen, preferably in an inactivated or attenuated form, an extract of the pathogen or an immunogenic protein of the pathogen.

More preferably, the antigen is an immunogenic protein that is expressed in and recovered from in vitro cultured cells.

In particular, the first antigen may be an antigen of a pathogen that induces (by natural exposure or by vaccination) pathogen specific antibodies of high prevalence in a particular animal species.

For example, this pathogen may be selected from the group existing of porcine circovirus type 2 (PCV-2), *Erysipelothrix rhusiopathiae*, bluetongue virus, border disease virus, *neospora canium*, turkey coronavirus and foot-and-mouth disease virus.

In particular, the second antigen may be an antigen of a pathogen that depends for its culturing in vitro on serum from a particular animal species.

For example, this pathogen may be selected from the group consisting of *Mycoplasma, Lawsonia, Leishmania, Babesia, Toxoplasma* and *Neospora*.

In a particularly preferred method according to the invention the first antigen is a porcine circovirus type 2 (PCV-2) antigen, in particular a PCV-2 ORF2 antigen.

The PCV-2 ORF2 antigen to be used in a method according to the invention represents a protein of about 30 kDa and is used as an active component in PCV2 vaccines commercially available, such as Porcilis PCV® (Intervet/Schering-Plough Animal Health, Netherlands). Ingelvac®CircoFLEX (Boehringer Ingelheim Vetmedica Inc., USA) and Suvaxyn PCV® (Fort Dodge Animal Health, USA). PCV-2 ORF2 to be used in a method according to the invention can, for example, be obtained from in vitro cultured insect cells infected with recombinant baculoviruses that are transformed with a gene encoding the PCV-2 ORF2 protein and that express the protein in the insect cells (Fort et al., Vaccine 27, 4031-4037, 2009; Nawagitgul et al., J. Gen. Virol. 81, 2281-87, 2000 and Fachinger et al., Vaccine 26, 1488-99, 2008).

In another preferred method according to the invention as described above the second antigen is *Mycoplasma hyopneumoniae* (M. hyo) and the composition comprising the second antigen additionally comprises serum, in particular serum antibodies directed against the first antigen and capable of binding thereto.

In a particularly preferred method according to the invention, the first antigen is a PCV-2 antigen, preferably, a PCV-2 ORF2 protein and the second antigen is a *M. hyo* antigen, preferably a *M. hyo* bacterin.

In essence, the method of the invention comprises a pre-treatment of the mixture comprising the antigen to be analysed before the antigen content thereof is determined in a conventional immunoassay. This pre-treatment involves the dissociation of the antigen-antibody complexes formed between the first antigen and antibodies that are capable of binding with this first antigen. The inventors have shown that such a dissociation step makes the first antigen available again for the quantification in an immunoassay.

Both in the field of human- and animal health it is common to manufacture combination vaccines comprising more than two different antigens. In particular, in the field of animal health combination vaccines comprising three to six different antigens is not unusual. Therefore, the method of the present invention also contemplates the determination the antigen content of a first antigen in a mixture that is composed of more than two compositions comprising different antigens, in particular three to six compositions.

A particularly suited method according to the invention as described above comprises the well known ELISA as the immunoassay.

In an exemplifying ELISA to be used in a method according to the invention as described above, the following steps are used:

coating the wells of an ELISA micro-titre plate with a capture antibody, preferably a monoclonal antibody, directed to the first antigen, incubating (serial dilutions of) a test sample of the mixture to be analysed, alongside a (series of dilutions of a) reference standard, and the appropriate control solutions, in the wells, incubating the wells with a detecting antibody, preferably a monoclonal antibody, directed to the first antigen. The detecting antibody may be directly, preferably indirectly, labelled with an enzyme. Preferably, the detecting antibody is a biotinylated antibody.

in case of indirect labelling, incubating the wells with an enzyme-conjugate that binds the enzyme to the antibody. Preferably, the conjugate is an avidin-enzyme conjugate, adding an enzyme substrate solution to the wells, followed by chromophoric detection. The amount of antigen in the test sample is calculated against the reference standard. A more detailed ELISA procedure is described in the Examples.

Typically, the enzyme used herein is horseradish peroxidase and the enzyme substrate is TMB (3,3',5,5' tetramethylbenzidine).

The method according to the invention can be used to determine the potency of a certain antigen in a mixture at various stages in the process of the manufacturing of a combination vaccine. For example, the method can be applied on a sample of a mixture that is composed of two or more compositions comprising the antigens, directly harvested from the culture vessel.

Alternatively, the compositions comprise the antigens in a further purified form, e.g. by means of centrifugation, filtration or precipitation.

Ideally, the potency of an antigen in a vaccine is determined in the final vaccine formulation, in its ready-to-use form. A ready-to-use vaccine formulation comprises all the components and excipients that are necessary and sufficient to allow the vaccine to be used in the field. In particular, a ready-to-use vaccine comprises two or more antigens, an adjuvant, a stabilizer and a preservative.

Therefore, in a preferred method according to the invention as described above, the mixture is a ready-to-use vaccine formulation.

In a particularly preferred method according to the invention as described above, the mixture is incubated with an acid solution to dissociate the antigen-antibody complexes.

In this pre-treatment step the mixture is diluted with the acid (dissociation) solution, optionally as a buffer, such as a PBS buffer or Tris-HCl buffer, and incubated to allow the antigen-antibody complexes to dissociate. The incubation can take place at room temperature under light shaking. After the pre-treatment step a sample of the acid treated mixture is analysed in an immunoassay, preferably by adding a sample of the acid treated mixture to an ELISA plate and further testing as described above.

It has been found that the nature of the acid solution is not critical. The examples show that a variety of acid solutions are able to dissociate the antigen-antibody complexes, and, at the same time leaving the antigenicity of the antigen unaffected.

In yet a further preferred method according to the invention as described above the acid solution is an acetic acid solution, sulphuric acid solution, hydrochloric acid solution or citric acid solution, preferably the acid solution is a citric acid solution.

In an alternative method according to the invention as described above the acid solution is a buffer.

The incubation time of the mixture with the acid solution may vary with the nature of the antigen in the antigen-antibody complex. Preferably, the incubation time is at least 8 hours, preferably 8-18 hours, more preferably 16-18 hours with a ready-to-use vaccine.

Thus, in another preferred method according to the invention as described above the mixture is incubated with an acid solution for at least 8 hours.

It has also been found by the inventors that the ratio (v/v) between the acid solution and the mixture may affect the level of dissociation of the antigen-antibody complexes. Good results have been obtained with a ratio (v/v) between the acid solution and the mixture of at least 25, in particular with a ratio (v/v) of 25-75, more in particular with a ratio (v/v) of 25-50.

Thus, in another preferred method according to the invention as described above the mixture is incubated at a ratio (v/v) between the acid solution and the mixture of at least 25, preferably 25-75, more preferably 25-50.

In a further preferred method according to the invention as described above the acid solution has a pH of 1.0-3.0, preferably of 1.5 (±0.2).

Optionally, in a method according to the invention as described above, after the incubation of the mixture with the acid solution, but before the analysis thereof in the immunoassay, the pH of the acid treated mixture is elevated to a more neutral pH, preferably 5-7. This can be done by adding a base solution or a buffer to the acid treated mixture. Appropriate solutions for this purpose are sodium hydroxide, phosphate- or Tris buffer.

The invention also is directed to a method for the determination of an antigen content of a PCV-2 antigen in a mixture of at least a composition comprising the PCV-2 antigen and a composition comprising a *M. hyo* antigen, the method comprising the steps of, A mixing the two compositions, and B determining the antigen content of the PCV-2 antigen by means of an immunoassay, characterized in that the *M. hyo* antigen is obtained from a culture that comprises non-swine serum.

In particular, the *M. hyo* antigen is obtained from a culture that comprises bovine-, horse, or sheep serum (Ahmad et al., Avian diseases 32, 519-526, 1988; Ramirez et al., 178, 149-152, 2008).

In a further alternative method the composition comprising the second antigen and the antibodies directed against the first antigen is subjected to a separation of these two components after which the composition comprising only the second antigen is mixed with the composition comprising the first antigen. Subsequently, the antigen content of the first antigen is determined by means of the immunoassay.

Therefore, the invention also relates to a method for the determination of an antigen content of a first antigen in a mixture of at least a composition comprising the first antigen and a composition comprising a second antigen, the method comprising the steps of, A separating the second antigen from antibodies that are capable of binding with the first antigen in a composition comprising the second antigen and the antibodies, B mixing the second antigen with a composition comprising the first antigen, and C determining the antigen content of the first antigen in the mixture by means of an immunoassay.

The separation of the second antigen from e.g. medium in which the antigen was cultured can be carried out by routine methods available for this purpose. For example, in case the second antigens are bacteria, these can be separated by means of centrifugation at 15.000 g for 10 minutes.

It is also possible that the separation is routinely effected by means of immuno-depletion wherein the antibodies are captured with a ligand that exhibits affinity for the antibodies, followed by a separation of these ligand-antibody complexes from the second antigen. Ligands commonly used for this purpose are Protein-G, Protein-A or antibodies directed against the antibodies to be separated. Usually, these ligands are bound to a solid phase (e.g. Sepharose 4B) that facilitate the separation of the antigen from the antibodies.

Therefore, in a preferred embodiment of this method the separation is effected by means of a centrifugation- or immuno-depletion step.

In further preferred embodiments of this method the antigens to be used and the immunoassay to be applied herein are the same as those defined above.

The invention is directed also the any of the methods as described above, further characterized in that the method is a potency test of a combination vaccine.

A potency test of a vaccine is defined as a test to determine the specific ability or capacity of the vaccine, as indicated by appropriate laboratory tests or by adequately controlled clinical data obtained through the administration of the vaccine in the manner intended, to effect protective immunity. As such, the potency test used in this invention is a test applied on a batch of vaccine produced for commercial purpose to provide data that show whether the batch of vaccine meets critical assay parameters.

In a preferred potency test according to the present invention the immunoassay is an ELISA (as outlined above) and the critical assay parameter is the antigen mass of the first antigen in the mixture expressed in ELISA-units (EU). The EU relate to an internal standard of the antigen that, in turn, correlates to protective immunity in a target animal.

EXAMPLES

Example 1 Influence of *M. hyo* Composition on the Quantification of PCV-2 Antigen in ELISA As a means of quality control concentrations of PCV2 containing vaccines are determined in a sandwich ELISA based on two monoclonal antibodies specific for PCV2.

However, as compared with monovalent vaccines, concentrations distinctly below the expectations were measured in bivalent vaccines comprising PCV2 and *Mycoplasma hyopneumoniae* (*M. hyo*) preparations.

A combination vaccine containing *M. hyopneumoniae* and PCV2 antigens was produced as follows: *M hyopneumoniae* whole cell antigen is produced by culturing *M. hyopneumoniae* strain 11 in a broth medium based on the medium originally described by Friis (Nord. Vet.-Med., 27, 337-339, 1975). This is a complex medium that contains yeast extract, serum and various extracts of porcine and bovine origin. At the end of cultivation, the bacterial cells were inactivated and the whole culture was concentrated at least 10 times by ultrafiltration and used for the formulation of the vaccine. The PCV2 ORF2 antigen was produced recombinantly using Baculo virus expression in *Sporoptera frugiperda* (Sf21) cells that were cultured in medium suitable for insect cell growth. After harvesting of the viral fluids, and inactivation of the virus particles, the PCV2 ORF2 antigen were concentrated by centrifugation and used for vaccine production. To prepare the combination vaccine, the two antigens were mixed, diluted with buffer and blended with the w/o adjuvant Xsolve (vitamin E acetate/light liquid paraffin/Tween 80) at a ratio of 70/30 (v/v).

A summary of the results from mixing the PCV2 preparations with placebo or several batches of *M hyo* preparations are shown in Table 1.

TABLE 1

Influence of Mhyo on the quantification of PCV by ELISA

| ELISA | PCV batch #1 | | PCV batch #2 | | PCV batch #3 | |
|---|---|---|---|---|---|---|
| | units[a] | recovery (%)[b] | units | recovery (%) | units | recovery (%) |
| — | 2961 | 100 | 2765 | 100 | 2482 | 100 |
| M hyo batch # 1 | 1109 | 37.5 | 1607 | 58.1 | 1627 | 65.6 |
| M hyo batch # 2 | 960 | 32.4 | 1641 | 59.3 | 1838 | 74.1 |
| M hyo batch # 3 | 939 | 31.7 | 2171 | 78.5 | 1983 | 79.9 | a) PCV concentrations are determined by comparing titrations of reference preparation and test samples by ELISA. To this end 96 well Nunc MaxiSorp plates are incubated over night at 4° C. with an optimal concentration of monoclonal antibody 3/1B4-INT diluted in carbonate buffer pH 9.6., serial dilutions of references and test samples, diluted in PBS containing BSA and Tween (EIA buffer), are incubated for 1 hour at 37° C. Followed by a wash step, an optimal concentration of biotin labeled monoclonal antibody 5/6H12-INT diluted in EIA buffer is incubated for 1 hour at 37° C. Followed by a wash step, an optimal concentration of HRP-labeled avidin diluted in EIA buffer is incubated for 0.5 hour at 37° C. Followed by a wash step, an optimal concentration of TMB substrate is incubated for 15 minutes and stopped by sulfuric acid and optical densities are measured with an ELISA reader. Concentrations are calculated by the 4PL method. Values are expressed as ELISA units (average of 3 measurements).

b) Standard deviation (n=3)

c) Recovery (%) as compared with vaccines containing the same amount of PCV in the absence of *M hyo*.

These results show that in vaccines containing PCV and *M hyo*, *M hyo* negatively affects the detectability of the PCV-2 antigen in the combination vaccine and that the degree of recovery (31%-80%) depends on the combination of the mixed PCV-2 and *M hyo* preparations.

Example 2 Identification of Antigen-Antibody Complexes

Figure 1:
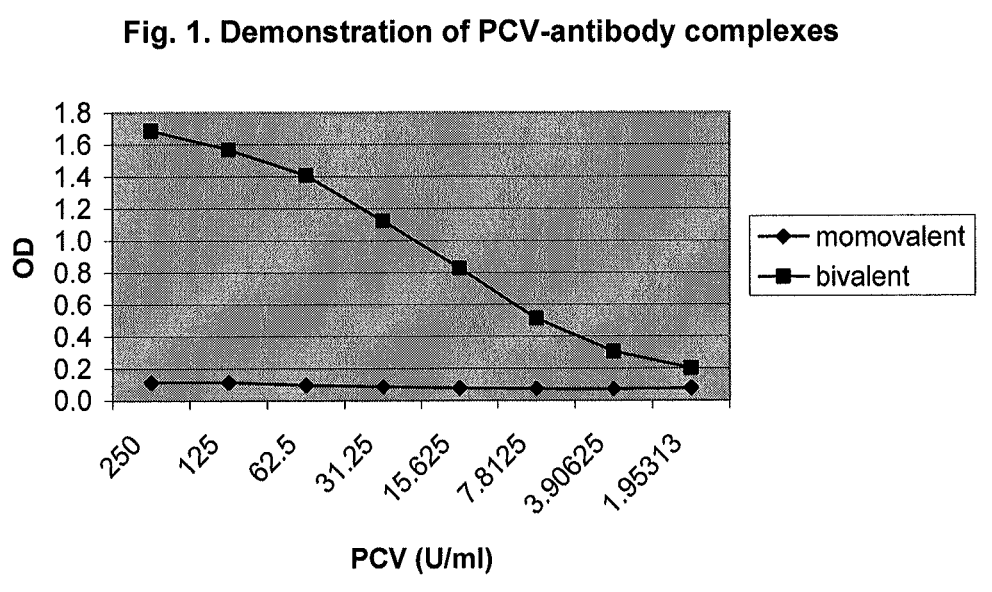

Antigen-antibody complexes in bivalent PCV-2/*M. hyo* vaccines have been demonstrated by a sandwich ELISA. Complexes between PCV-2 antigen and polyclonal porcine anti-PCV-2 antibodies are captured by monoclonal anti-PCV-2 antibodies coated to microtiter plate wells and detected with enzyme labelled anti-porcine IgG conjugate. FIG. 1 shows a titration of a monovalent vaccine containing PCV-2 and of a bivalent vaccine containing PCV-2 and *M. hyo*. The ELISA was performed as described in Example 1 with the exception that instead of a labelled monoclonal anti-PCV antibody, complexes were detected with an enzyme labelled anti-porcine IgG conjugate. Data points represent the average of triplicates. The results demonstrate that a) the *M. hyo* preparations contain porcine anti-PCV-2 antibodies and b) that these antibodies form complexes with PCV-2.

The most likely explanation for reduced detectability of PCV-2 in bivalent vaccines is that the porcine anti-PCV-2 antibodies block PCV-2 epitopes relevant in the PCV-2 sandwich ELISA. PCV-2 antibodies were found to be present in commercial swine serum batches necessary in the medium used in the media for culturing *M. hyo* for manufacturing vaccines on a commercial scale.

Example 3 Attempts to Reverse the Inhibitory Effect of *M Hyo*

Procedures to reverse the inhibitory effect of *M hyo* preparations were tested by treating two vaccine preparations containing the same amount of PCV-2 but lacking (monovalent vaccine) or containing (bivalent vaccine) *M. hyo*. The sandwich ELISA, as described in Example 1, was performed either in the presence of various concentrations of reagents (SDS, Tween Triton, Na deoxycholate, Urea) in the diluent. Furthermore, supernatants and pellets of ammonium sulphate (AS) precipitations (without or in the presence of Triton) and size separated fractions (in the presence of Triton) were assayed.

TABLE 2

Effect of vaccine treatments

| treatment | concentration range | recovery (%) monovalent | bivalent |
|---|---|---|---|
| — | | 100 | 33.9 |
| SDS (%) | 0.25-2 | 72-167 | 24-48 |
| Tween (%) | 0.1-5.4 | 106-116 | 26-30 |
| Triton X100 (%) | 0.1-5.4 | 113-119 | 32-35 |
| Na deoxychol. (%) | 0.1-5.4 | 113-129 | 31-44 |
| Urea (M) | 1-8 | 0-101 | 0-47 |
| AS precipitation (%), supernatant | 2.5-80 | ND | 3-37 |
| AS precipitation (%), pellet | 2.5-80 | ND | 0.2-7.6 |
| 2% SDS, AS precipitation (%), supernatant | 2.5-80 | 2.7-16 | 0.1-25 |
| 2% SDS, AS precipitation (%), pellet | 2.5-80 | 6.6-17 | 0.4-16 |
| 10% Triton X100, filtration >300 kD | | 56 | 9 |
| 10% Triton X100, filtration <300 kD | | 3 | 1 |

The results of Table 2 show that none of the treatment left the monovalent vaccine unaffected and reversed the inhibitory effect of *M hyo*.

Example 4: Effect of Acid Treatment on Viral Antigen-Antibody Complexes

The potential of acid treatments has been evaluated. One part (volume) of vaccine is mixed with 49 parts of 0.1M citric acid (diluted in distilled water) and incubated over night at room temperature with light shaking Representative results generated with a developed standard procedure are shown in Table 3.

TABLE 3

Effect of acid treatment

| | Acid treatment[c] | PCV batch #1 units[a] | recovery (%)[b] | PCV batch #2 units | recovery (%) | PCV batch #3 units | recovery (%) |
|---|---|---|---|---|---|---|---|
| — | − | 2961 | 100 | 2765 | 100 | 2482 | 100 |
| | + | 3273 | 100 | 2941 | 100 | 3430 | 100 |
| M hyo batch # 1 | − | 1109 | 37.5 | 1607 | 58.1 | 1627 | 65.6 |
| | + | 3061 | 93.5 | 2844 | 96.7 | 3110 | 90.7 |
| M hyo batch # 2 | − | 960 | 32.4 | 1641 | 59.3 | 1838 | 74.1 |
| | + | 3124 | 95.4 | 2760 | 93.8 | 2950 | 86.0 |
| M hyo batch # 3 | − | 939 | 31.7 | 2171 | 78.5 | 1983 | 79.9 |
| | + | 3247 | 99.2 | 2875 | 97.8 | 3468 | 101.1 |

[a]-[c]as described in Example 1

The results in Table 3 demonstrate that the inhibitory effect of M. hyo preparations can be reversed by the acid treatment.

Example 5: Effect of Acid Treatment on Bacterial Antigen-Antibody Complexes

To demonstrate the effect of acid treatment on bacterial antigen-antibody complexes a component (*Leptospirae tarassovi*) of a canine vaccine against leptospirosis was quantified in a sandwich ELISA comparable to that of the PCV-2 ELISA in the presence and absence of artificially added polyclonal canine serum antibodies containing *L. tarassovi* specific antibodies, with or without acid treatment.

TABLE 4

Detection of bacterial antigen and antigen-antibody complexes by ELISA a)

| Treatment | A | B | C | D |
|---|---|---|---|---|
| Inc. of polycl. Porc. anti-tarassovi antibodies | − | + | − | + |
| Acid treatment | − | − | + | + |
| ELISA (% of control) | 100 | 50.9 ± 2.1 | 93.8 ± 1.8 | 99.2 ± 3.6 | a) L. tarassovi antigen was quantified by ELISA essentially as described in Example 1 using tarassovi specific monoclonal antibodies (A). Canine serum containing polyclonal anti-tarassovi antibodies and antigen were incubated prior to antigen quantification by ELISA (B, D). Acid treatment was performed as described in Example 4. ELISA results were expressed as % of the control experiment (A). Values are the mean ± Std of duplicates.

These results demonstrate that that the inhibitory affect of canine serum antibodies on the quantification of bacterial vaccine components by ELISA can be reversed by an acid treatment.

Example 6: Parameters Affecting the Acid Treatment 5.1. Capacity of Different Acids and Base The effect of several acids and base on the determination of the antigen content in vaccine preparations are summarized in Table 5.

TABLE 5

Treatment with different acids and sodium hydroxide

| Treatment[a] | Citric acid recovery (%) | Acetic acid recovery (%) | Sulfuric acid recovery (%) | Hydrochloric acid recovery (%) | Sodium hydroxide recovery (%) |
|---|---|---|---|---|---|
| ELISA[b] | 97[c] | 94 | 98 | 128 | 0[d] |

[a]Bivalent vaccine preparations were treated as described in Example 4 with the exception that all acids had been adjusted to pH 1.5 and sodium hydroxide to pH 13.5
[b]PCV concentrations were determined by ELISA as described in Example 1
[c]recovery is expressed as the percentage of the concentration measured as compared to the concentration without treatment
[d]No detectable PCV by ELISA These results demonstrated that the inhibitory effect of *M. hyo* is independent from the type of acid used.

Treatment with sodium hydroxide at pH 13.5 completely abolished the detection of PCV-2 antigen by ELISA. This is likely due to a destruction of the PCV-2 epitopes recognized by the monoclonal antibodies used in the ELISA.

5.2. Influence of Acid Concentration

The influence of acid concentration was tested by varying the ratio (v/v) between 0.1M citric acid and monovalent or bivalent vaccine. See FIG. 2, where a) Recovery (%) based on untreated monovalent vaccine measured by ELISA as described in Example 1.

b) Ratio (v/v) between acid and vaccine during the acid treatment as described in Example 4. The results in FIG. 2 demonstrate that a low recovery rate of a bivalent vaccine can be overcome by acid treatment with a ratio 5.3 Influence of Treatment Time The influence of treatment time is shown in FIG. 3, where a) Units/ml determined by ELISA as described in Example 1. The results indicate that a treatment hours is necessary for a sufficient degree of inhibition reversal.

5.4. Influence of pH

The influence of pH was assessed by acid treatments at different pH's. In FIG. 4, a) 5 independent PCV batches were each mixed with one out of two (A, B) independent *M hyo* batches. All 10 preparations were acid treated as described in Example 4 either with 0.1M citric acid or with 0.1M citric acid adjusted with sodium acetate to pH 2, 3, 4, or 5, or with buffer (C=control). The concentrations are expressed as percentages of the concentrations obtained by the standard treatment (0.1M citric acid, pH 1.5). Data are shown as the mean±Std of the 5 PCV batches combined either with *M hyo* batch A or B.

These data show that acid treatment at a pH≤3 results in a significant reversal of the inhibitory effect of *M. hyo* preparations.

The invention claimed is:

1. A ready to use vaccine comprising a porcine circovirus type 2 (PCV-2) antigen and a *Mycoplasma hyopneumoniae* (*M. hyo*) antigen;
    wherein the *M. hyo* antigen originates from media comprising serum that also contains an antibody that is capable of binding to the PCV-2 antigen; wherein the *M. hyo* antigen has been separated from said antibody; and wherein said composition is obtained by the method of:
    A. separating the *M. hyo* antigen from said antibody by either centrifugation or an immuno-depletion step; wherein the *M. hyo* antigen is separated from said antibody; and
    B. mixing the PCV-2 antigen with the *M. hyo* antigen separated from said antibody.

2. The ready to use vaccine of claim 1, wherein the PCV-2 antigen is a PCV-2 ORF2 protein, the *M. hyo* antigen is a bacterin, or both the PCV-2 antigen is a PCV-2 ORF2 protein and the *M. hyo* antigen is a bacterin.

3. The ready to use vaccine of claim 2, wherein the *M. hyo* antigen is an *M. hyo* bacterin and the PCV-2 antigen is a PCV-2 ORF2 protein.

4. The ready to use vaccine of claim 2, wherein said separating of the *M. hyo* antigen from said antibody is performed by an immuno-depletion step.

5. The ready to use vaccine of claim 4, wherein said immuno-depletion step is performed with a Protein-G ligand or a Protein-A ligand.

6. The ready to use vaccine of claim 5, wherein the Protein-G ligand or the Protein-A ligand is bound to a solid phase.

7. The ready to use vaccine of claim 5, wherein said immuno-depletion step is performed with the Protein-A ligand.

8. The ready to use vaccine of claim 7, wherein the Protein-A ligand is bound to a solid phase.

9. A ready to use vaccine comprising a porcine circovirus type 2 (PCV-2) antigen and a *Mycoplasma hyopneumoniae* (*M. hyo*) antigen; wherein the *M. hyo* antigen originates from media comprising serum that also contains an antibody that is capable of binding to the PCV-2 antigen; and wherein the *M. hyo* antigen had been separated from said antibody prior to mixing the *M. hyo* antigen with the PCV-2 antigen to form said ready to use vaccine.

10. The ready to use vaccine of claim 9, wherein the PCV-2 antigen is a PCV-2 ORF2 protein, the *M. hyo* antigen is a bacterin, or both the PCV-2 antigen is a PCV-2 ORF2 protein and the *M. hyo* antigen is a bacterin.

11. The ready to use vaccine of claim 10, wherein the *M. hyo* antigen is an *M. hyo* bacterin and the PCV-2 antigen is a PCV-2 ORF2 protein.

12. The ready to use vaccine of claim 10, wherein said separating of the *M. hyo* antigen from said antibody is performed by an immuno-depletion step.

13. The ready to use vaccine of claim 12, wherein said immuno-depletion step is performed with a Protein-G ligand or a Protein-A ligand.

14. The ready to use vaccine of claim 13, wherein the Protein-G ligand or the Protein-A ligand is bound to a solid phase.

15. The ready to use vaccine of claim 12, wherein said immuno-depletion step is performed with the Protein-A ligand.

16. The ready to use vaccine of claim 15, wherein the Protein-A ligand is bound to a solid phase.

* * * * *